United States Patent [19]

Burns et al.

[11] Patent Number: 5,279,797
[45] Date of Patent: Jan. 18, 1994

[54] DISPOSABLE LIQUID REAGENT CARTRIDGE AND RECEPTACLE THEREFOR

[75] Inventors: Rickey D. Burns, Alpharetta; Bernhard H. Heitz, Woodstock; Drew F. Meincke, Lawrenceville; Karl H. Wentzel, Roswell, all of Ga.

[73] Assignee: AVL Scientific Corporation, Roswell, Ga.

[21] Appl. No.: 956,263

[22] Filed: Oct. 5, 1992

[51] Int. Cl.$^5$ .............................................. B01L 11/00
[52] U.S. Cl. ......................................... 422/102; 422/61; 422/63; 422/65; 422/103; 206/221; 220/403; 220/404
[58] Field of Search ................ 422/61, 63, 65, 102, 422/103; 222/94, 95, 132, 325; 206/219, 221, 438; 220/403, 404, DIG. 908

[56] References Cited

U.S. PATENT DOCUMENTS

| | | | |
|---|---|---|---|
| 3,718,439 | 2/1973 | Rosse et al. | 422/102 |
| 3,963,148 | 6/1976 | Proni et al. | 422/63 X |
| 4,116,336 | 9/1978 | Sorensen et al. | 422/61 X |
| 4,178,345 | 12/1979 | Terk | 422/61 |
| 4,195,060 | 3/1980 | Terk | 422/61 |
| 4,328,185 | 5/1982 | Reasons et al. | 422/82 |
| 4,390,499 | 6/1983 | Curtis et al. | 422/72 |
| 4,548,606 | 10/1985 | Larkin | 604/414 |
| 4,570,827 | 2/1986 | Roggenburg et al. | 222/95 |
| 4,588,554 | 5/1986 | Kaartinen et al. | 422/61 |
| 4,691,845 | 9/1987 | Schwartz | 222/94 |
| 4,693,867 | 9/1987 | Commarmot et al. | 422/64 |
| 4,796,788 | 1/1989 | Bond | 222/94 |
| 4,869,398 | 9/1989 | Colvin et al. | 222/83 |
| 4,889,692 | 12/1989 | Holtzman | 422/102 |
| 4,970,053 | 11/1990 | Fechtner | 422/102 |
| 5,031,797 | 7/1991 | Boris et al. | 222/23 |
| 5,075,082 | 12/1991 | Fechtner | 422/102 |
| 5,104,813 | 4/1992 | Besemer et al. | 436/179 |
| 5,115,943 | 5/1992 | Coleman | 222/94 |
| 5,132,026 | 7/1992 | Baluyot et al. | 210/767 |
| 5,135,497 | 8/1992 | Hessel et al. | 604/132 |
| 5,154,888 | 10/1992 | Zander et al. | 422/58 |
| 5,163,587 | 11/1992 | Apps et al. | 222/105 |

Primary Examiner—James C. Housel
Assistant Examiner—Harold Y. Pyon
Attorney, Agent, or Firm—Watson, Cole, Grindle & Watson

[57] ABSTRACT

A disposable liquid reagent cartridge for use with an analytical instrument includes a permanently closed hollow housing, a plurality of separate sealed flexible bags which are preformed independently of the housing and which are subject to damage and tampering if unprotected, at least some of the bags having reagents therein, the bags being supported in operative position within the housing, the housing being formed of the material sufficiently rigid to retain its outer shape and protect the bags supported therein from damage or tampering, connectors supported by the housing and being exposed to the exterior of the housing, and a flexible tube connected between each of the bags and the connectors to provide communication of the reagents between the bags and the connectors.

13 Claims, 4 Drawing Sheets

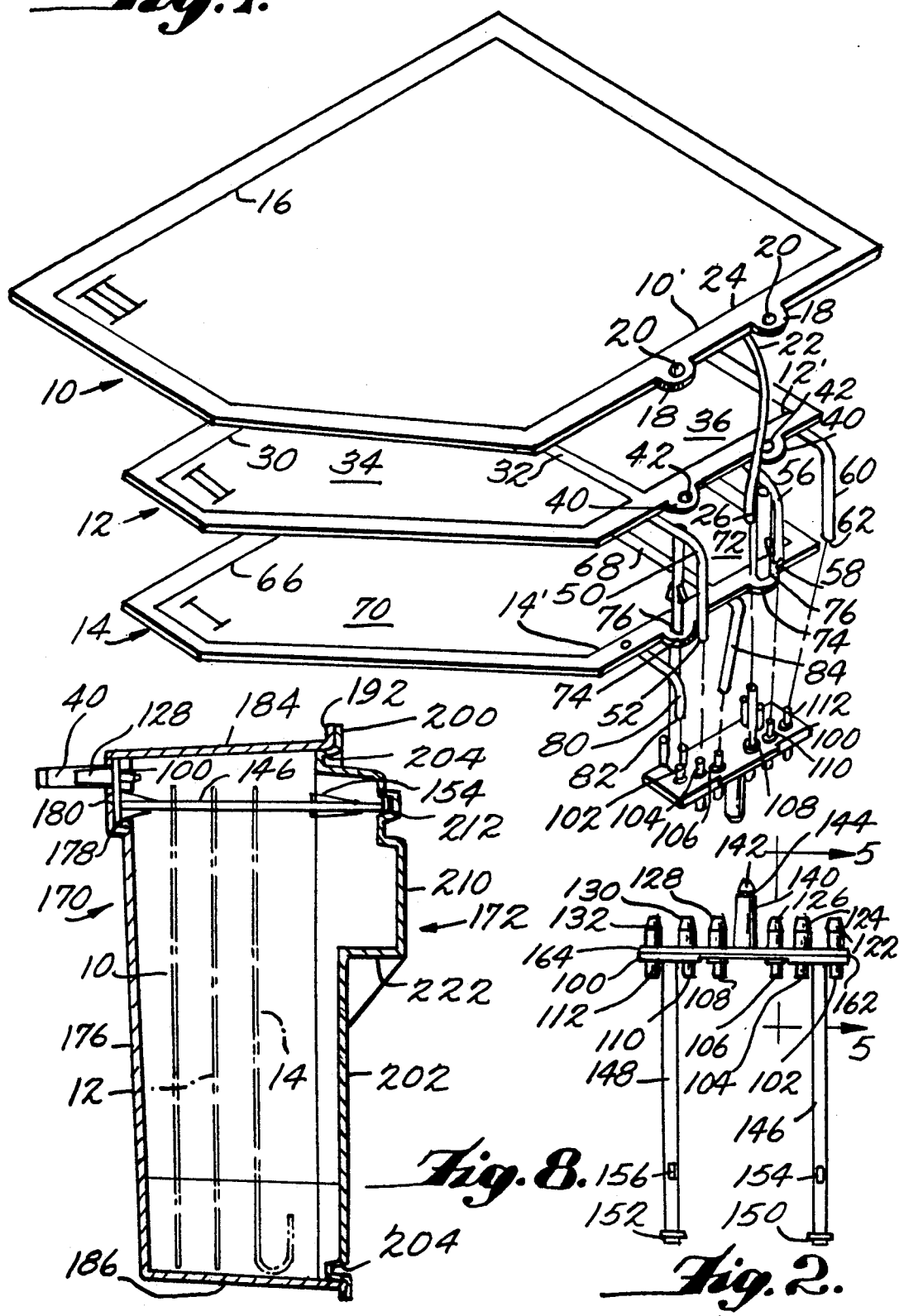

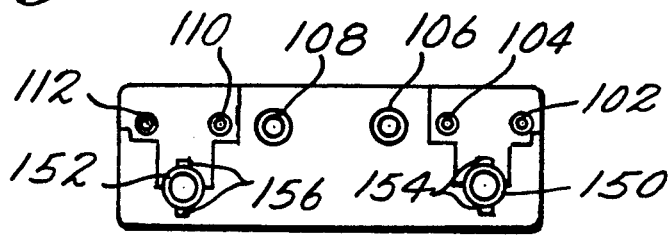
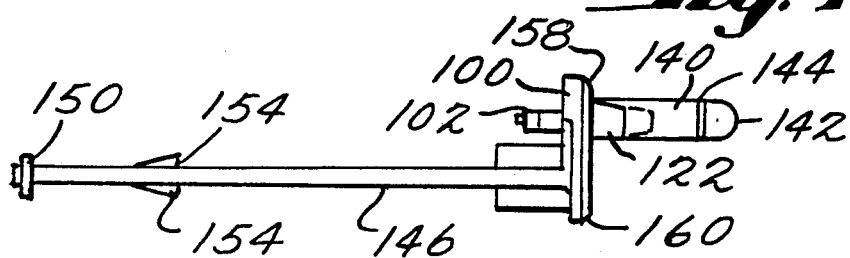
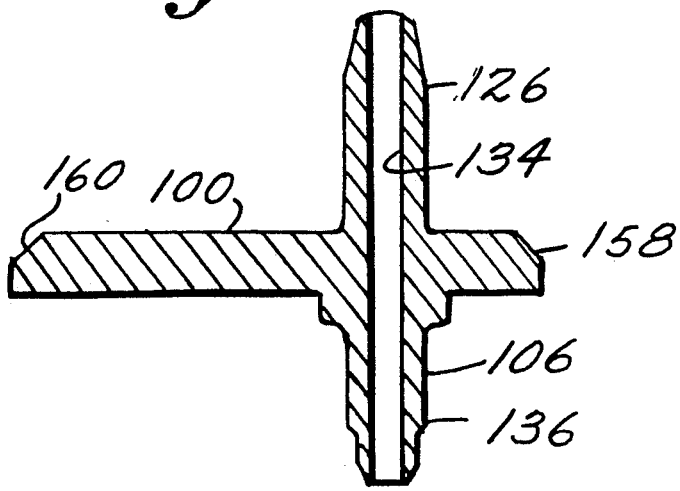
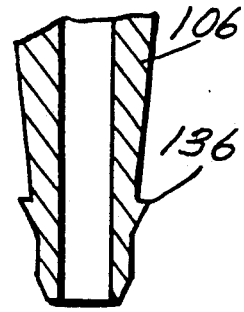
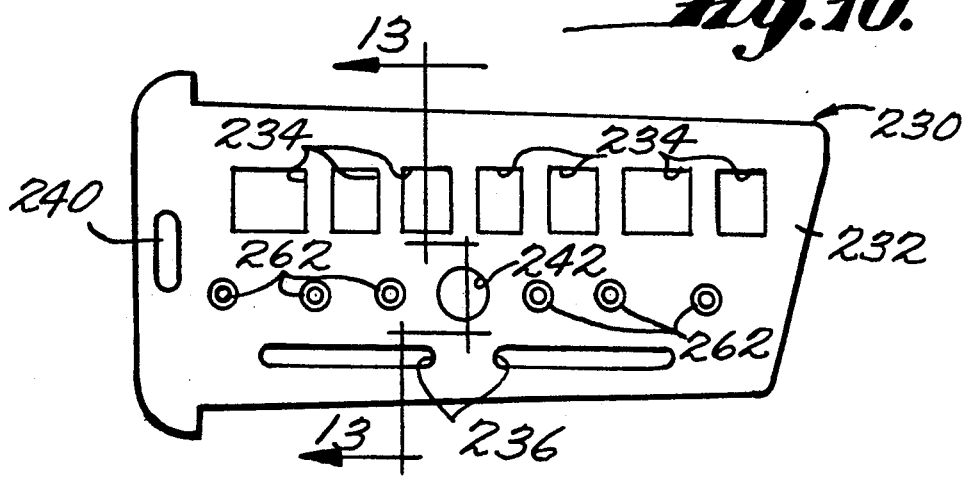

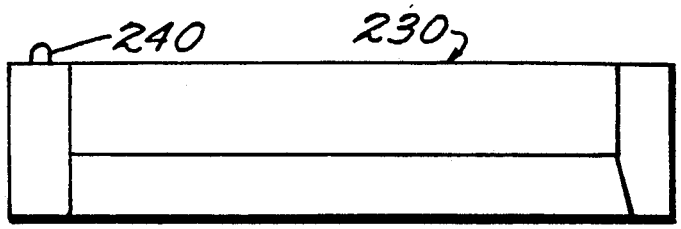
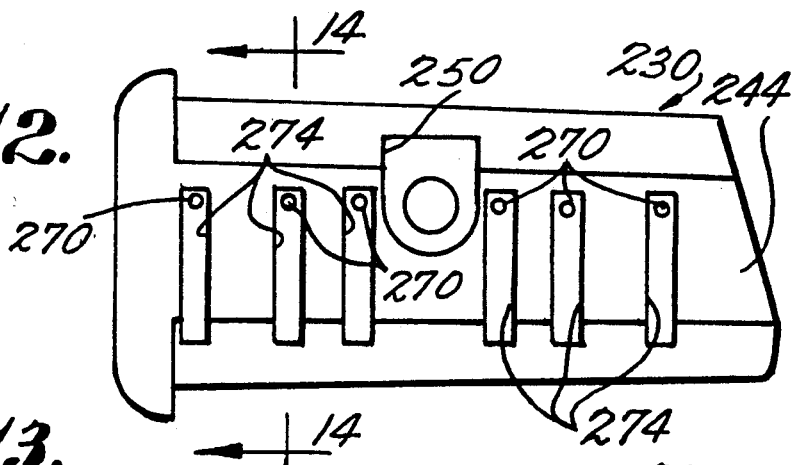
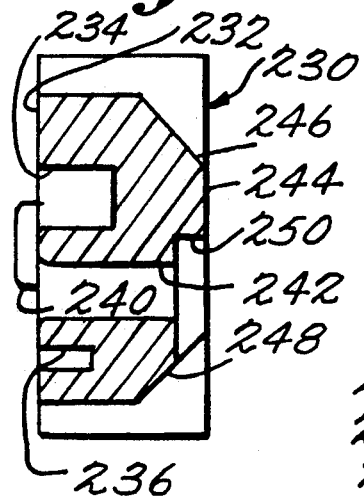
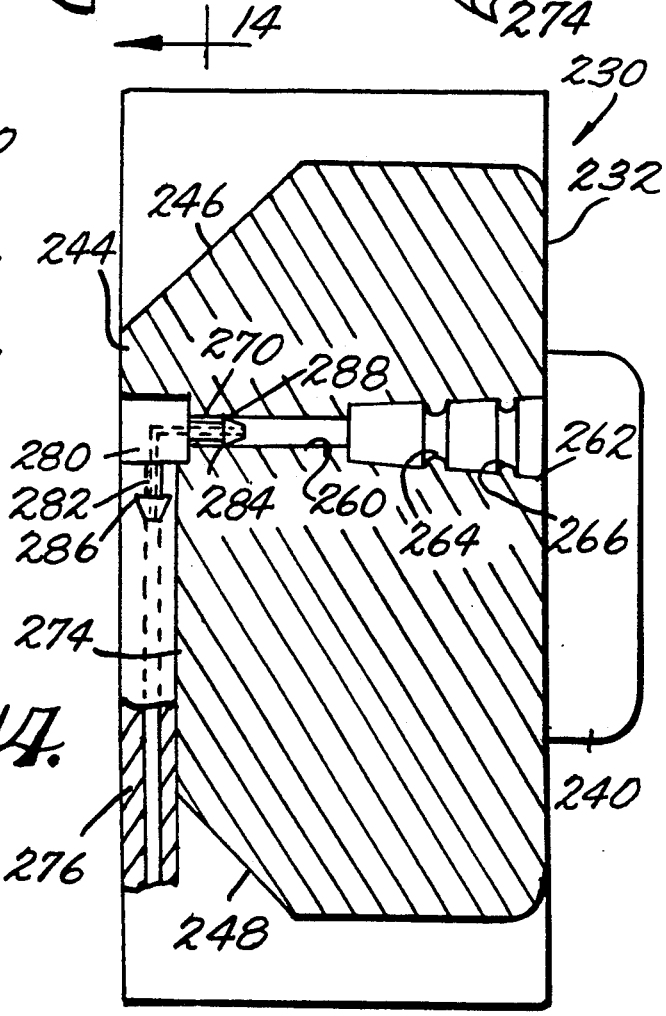

DISPOSABLE LIQUID REAGENT CARTRIDGE AND RECEPTACLE THEREFOR

BACKGROUND OF THE INVENTION

The present invention relates to a disposable cartridge having bag means therein which contains a plurality of reagents which are to be supplied to an analytical instrument such as an ion selective electrode electrolyte analyzer. These reagents are well-known in the art and are used with the measurement cell of an analyzer to analyze specific ions such as sodium, potassium and chloride of liquids such as serum and blood, for example.

In the prior art, sealed packages have been employed for supplying reagents and reference liquids to analyzers. U.S. Pat. Nos. 4,116,336 and 4,588,554 disclose such packages. When analyzing serum or blood, it is necessary to provide a number of different reagents as well as a reference solution. Accordingly, it is desirable to provide means for connecting a plurality of packages to the analyzer with minimum effort. This can be done by providing a combination package so that a plurality of packages can be readily connected to an analyzer. U.S. Pat. No. 4,588,554 discloses a combination package including bar-like connector banks each of which is connected to a number of different individual packages and which is also connected to the analyzer. The problem with such an arrangement is that the packages are not protected from damage or tampering, and furthermore, the overall arrangement is not readily mounted in operative position.

The prior art has also suggested the use of reagent cartridges wherein the reagents are housed within chambers formed in the cartridges, and the cartridges are then operatively connected with an analyzer. Such arrangements are shown for example in U.S. Pat. Nos. 4,195,060, 4,970,053 and 5,031,797. These patents disclose rather complex constructions wherein the cartridges include integral chambers for receiving the reagents. These complex constructions increases the expense of the cartridge and furthermore are excessively bulky. U.S. Pat. No. 4,869,398 discloses a liquid storage and dispensing system for use with various liquids. An inner bladder is disposed within a plastic bag and dispensing ports are connected with the bladder. This assembly is disposed within a cardboard box having a lid which can be opened to remove the liquid container which then can be hung up for use. Alternatively, a plurality of boxes can be stacked on one another. The liquid containers are not protected from damage or tampering, and it is apparent that assembly of a plurality of containers with respect to cooperating apparatus is rather complicated.

Accordingly, it is desirable to provide a cartridge having a plurality of bags therein which is relatively cheap to manufacture, and wherein the bags are protected from damage or tampering. Additionally, the cartridge should be capable of being mounted in operative position with a minimum of effort.

SUMMARY OF THE INVENTION

The invention includes a permanently closed hollow housing having a plurality of flexible bags supported therein and surrounded by the housing such that the bags are protected from damage and tampering. The bags may contain a single liquid, or more than one liquid may be disposed within separate sealed chambers formed in an individual bag. The outer configuration of the housing is complementary to a cavity in an analytical instrument so that the cartridge can be mounted in position by simply pushing the housing into the cavity.

Connector means is supported by the housing and is exposed to the exterior of the housing, flexible tube means being connected between the bags and the connector means. The connector means includes integral support rod means upon which the bags are supported.

A receptacle is provided for use with the cartridge and serves to provide liquid flow communication between the connector means of the cartridge and tubing connected to an analytical instrument. The receptacle includes a plurality of passages for receiving bosses formed on the connector means when the bosses are manually inserted into one end of the passages in the receptacle. A sealing means is provided at one end of the passages to prevent leakage of liquid. The opposite end of each of the passages in the receptacle is in communication with one of a plurality of grooves formed in the receptacle and which receive tubing connected to an analytical instrument. Elbow connectors are provided to provide a liquid-tight seal between the opposite ends of the openings in the receptacle and the associated tubing.

BRIEF DESCRIPTION OF THE DRAWINGS

FIG. 1 is a top perspective exploded view of a plurality of flexible bags and the flexible tubes connecting the bags to a connector means;

FIG. 2 is a top view of the connector means;

FIG. 3 is a back view of the connector means shown in FIG. 2;

FIG. 4 is a side view of the connector means shown in FIG. 2;

FIG. 5 is a sectional view on an enlarged scale taken along line 5—5 of FIG. 2;

FIG. 6 is an enlarged view of a portion of FIG. 5;

FIG. 8 is a sectional view taken along line 8—8 of FIG. 7;

FIG. 10 is a back view of a receptacle according to the invention;

FIG. 11 is a bottom view of the receptacle shown in FIG. 10;

FIG. 12 is a view showing the opposite side of the receptacle from that shown in FIG. 10;

FIG. 13 is a sectional view taken along line 13—13 of FIG. 10; and

FIG. 14 is a sectional view on an enlarged scale taken along line 14—14 of FIG. 12.

DESCRIPTION OF THE PREFERRED EMBODIMENT

Figure 9:
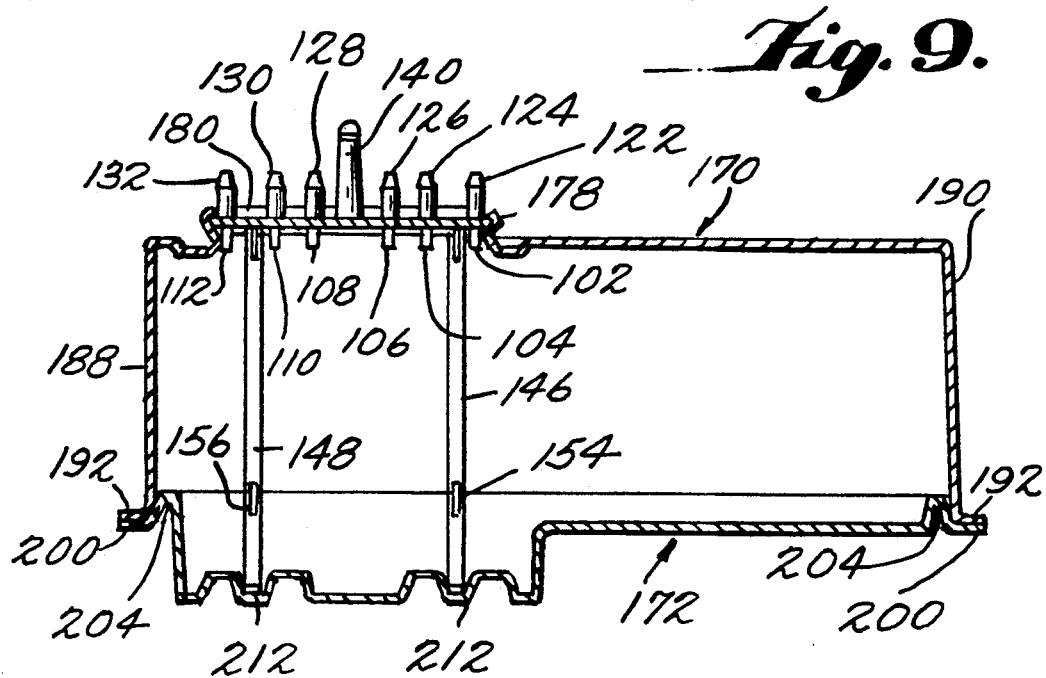
FIG. 9 is a sectional view taken along line 9—9 of FIG. 7.

Referring now to the drawings wherein like reference characters designate corresponding parts throughout the several views, there is shown in FIG. 1 three flexible bags indicated generally by reference numerals 10, 12 and 14 each of which has a shape similar to the internal shape of the housing hereinafter described, the outer configuration of the housing being shaped complementary to the shape of a cavity in an analytical instrument with which the cartridge is to be used.

It is noted that the number and type of bags utilized may vary from one application to another, and that the described arrangement is merely a typical arrangement used when analyzing serum or blood. The bag 10 is formed of polyethylene and is heat sealed along the periphery thereof as indicated by line 16. This is a liquid waste bag and may be provided with a conventional one-way flapper valve therein in the form of a pair of layers of material at the top of the bag which are adapted to separate and allow liquid to enter the bag, but which will be pressed together by pressure of liquid within the bag to prevent the flow of liquid waste out of the bag. A pair of support portions 18 are formed integral with the bag and include a pair of holes 20 therethrough for supporting the bag within the housing as hereinafter explained. A flexible tube 22 also formed of polyethylene has a first end 24 which is heat sealed within the sealed edge of the bag and which opens into the upper end of the bag as indicated at 10'. The opposite end of tube 22 terminates in an open end 26 adapted to be connected to the connector means hereinafter described.

The second bag 12 is formed of two layers of aluminum foil each of which is coated on both sides with a layer of polyethylene. The bag is sealed along the periphery thereof by heat sealing as indicated by line 30. The bag is further heat sealed along the portion 32 thereof from top to bottom of the bag to define a pair of separate sealed chambers therewithin as indicated by numerals 34 and 36. Bag 12 is provided with a pair of support portions 40 having holes 42 formed therethrough for supporting the bag in operative position.

A flexible tube 50 formed of polyethylene is heat sealed within the sealed edge of bag 12 and opens into the lower part of chamber 34. The opposite end of tube 50 terminates in an open end 52 adapted to be connected to the connector means. A tube 56 formed of polyethylene is heat sealed within the sealed edge of bag 12 and opens into the lower part of chamber 36. The opposite end of tube 56 terminates in an open end 58 adapted to be connected to the connector means. A flexible tube 60 formed of polyethylene has a one end 61 heat sealed within the sealed edge of bag 12 and opening into the upper part of chamber 36 as indicated at 12'. The opposite end of tube 60 terminates in an open end 62 adapted to be connected to the connector means.

The third bag 14 is also formed of two layers of aluminum foil each of which is coated on both sides with a layer of polyethylene. The bag is sealed along the periphery thereof by heat sealing as indicated by line 66. The bag is further heat sealed along the portion 68 thereof from top to bottom of the bag to define a pair of separate sealed chambers therewithin as indicated by numerals 70 and 72. Bag 14 is provided with a pair of support portions 74 having holes 76 formed therethrough for supporting the bag in operative position.

A flexible tube 80 also formed of polyethylene is heat sealed within the sealed edge of bag 14 and opens into the lower part of chamber 70. The opposite end of tube 80 terminates in an open end 82 adapted to be connected to the connector means. A flexible tube 84 formed of polyethylene is heat sealed within the sealed edge of bag 14 and opens into the lower part of chamber 72. The opposite end of tube 84 terminates in an open end 86 adapted to be connected to the connector means.

In a typical example, chambers 34, 70 and 72 are initially filled with liquid reagents. Chamber 36 is initially filled with a reference solution which is recycled between chamber 36 and the associated analytical instrument. Bag 10 is initially empty and is subsequently filled with waste liquid produced during the normal analyzing operations of the associated instrument.

It is noted that the reference solution disposed within chamber 36 should be electrically shielded, and the aluminum foil serves to provide the desired electrical shield. The aluminum foil surrounding the other chambers containing reagents serves to prevent evaporation of the reagents.

Referring to FIGS. 2 and 3, the construction of the connector means is illustrated. The connector means is an integral molded piece of relatively rigid unbreakable plastic material such as polycarbonate. The connector means includes a main body portion 100 having a first plurality of tapered bosses 102, 104, 106, 108, 110 and 112 extending from one side thereof. A second plurality of tapered bosses 122, 124, 126, 128, 130 and 132 are aligned with the first bosses and extend from the opposite side of body portion 100.

As seen in FIG. 5, a passage 134 is provided through aligned bosses 106 and 126. A similar passage is provided through each pair of aligned bosses. As seen in FIG. 6, boss 106 is provided with a peripheral sharp edge or barb 136 which is adapted to cooperate with the end of an associated flexible tube to hold the tube in place on the boss and to provide a liquid-tight seal therewith. All of the bosses are provided with similar barbs to form a liquid-tight seal when the tubes are forced onto the associated bosses.

As seen in FIGS. 2 and 4, an elongated nose portion 140 has a rounded outer end 142 for facilitating insertion and removal of the connector means relative to a cooperating receptacle hereinafter described. The nose portion has a peripheral groove 144 formed therearound to indicate that the connector means is properly seated in a cooperating receptacle.

A pair of support rods 146 and 148 extend from body portion 100 and serve to support the bags within the cartridge. The support rods have tapered outer ends 150 and 152 respectively to facilitate mounting of the bags on the support rods as the outer ends of the rods pass through the holes formed in the support portions of the bags. The support rods also include tapered retainer portions 154 and 156 respectively which extend from opposite sides of the rods. These retainer portions enable the bags to be easily slid into place on the rods, but prevent reverse movement of the bags so as to prevent the bags from moving off of the rods.

Referring back to FIG. 1, it is noted that end 82 of tube 80 is connected with boss 102 as indicated by the dotted lines. Similarly, end 54 of tube 50 is connected to boss 104; end 86 of tube 84 is connected to boss 106; end 26 of tube 22 is connected to boss 108; end 58 of tube 56 is connected to boss 110; and end 62 of tube 60 is connected to boss 112.

As seen in FIG. 5, body 100 also includes tapered edges 158 and 160 along the top and bottom edges thereof As seen in FIG. 2, body 100 also has tapered edges 162 and 164 formed along the side edges thereof. These tapered edges cooperate with the housing described below.

Figure 7:
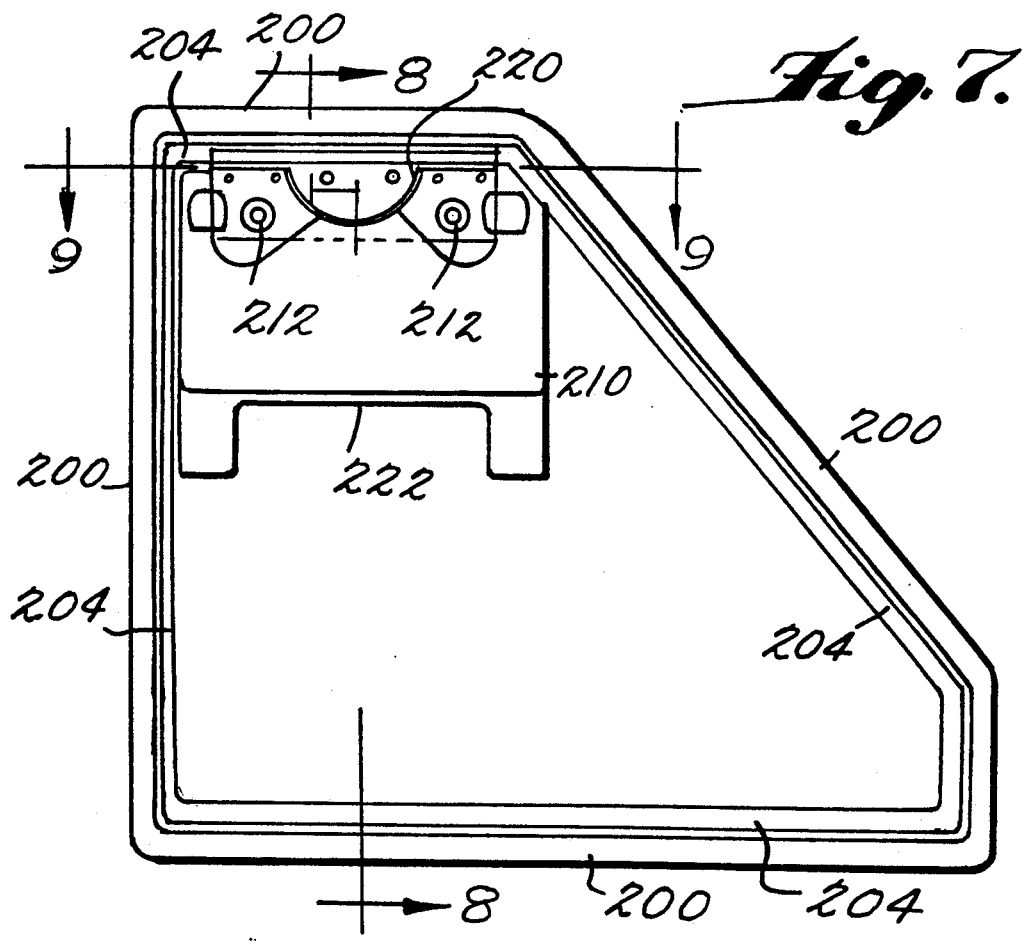
FIG. 7 is front view of the housing of the invention.

Referring now to FIGS. 7–9, the housing of the cartridge is illustrated, the housing being formed of a suitable plastic such as polyvinylchloride which is somewhat flexible, but sufficiently rigid to retain its outer shape and protect the bags supported therewithin. The housing includes an integral first housing portion 170 and a cover portion 172 which is permanently attached to the body portion. Body portion 170 includes a rear wall 176 having an outwardly extending generally rectangular portion 178 having an elongated slot 180 formed therethrough. The interior configuration and dimensions of the portion 178 are such that the body portion 100 of the connector means is adapted to snap into place within portion 178 with the tapered edges 158, 160, 162 and 164 disposed adjacent the inner walls of portion 178. The connector means is held in place with the tapered bosses 122, 124, 126, 128, 130 and 132 as well as the nose portion 140 extend outwardly through slot 180 to cooperate with a receptacle described hereinafter.

Housing portion 170 includes a top wall 184 and a bottom wall 186 which join with a pair of opposite side walls 188 and 190. A continuous peripheral flange 192 extends along the top wall, each side wall and the bottom wall. Lid 172 includes a continuous peripheral flange 200 formed around the periphery thereof and having an elevational configuration as seen in FIG. 7 which is identical to the configuration of flange 192 on housing portion 170.

The front wall 202 of the lid portion has a deformed part 204 immediately inwardly of the flange 192 and extending completely around the front wall as seen in FIG. 7. This deformed part fits snugly within the open end of housing portion 170 so that the deformed part serves to guide the lid portion into position during assembly of the cartridge with the deformed part frictionally engaging the inner surfaces of walls 184, 186, 188 and 190 of the housing portion. When the lid portion is assembled in the position shown in FIGS. 7-9, the flanges 192 and 200 are permanently bonded to one another by ultrasonic welding so that the housing is permanently closed to prevent access to the bags within the housing and thereby preventing tampering with the bags.

The wall 202 of the lid portion also includes an outwardly extending integral portion 210 which in turn has outwardly extending integral projections 212 each of which defines a recess therein for receiving the outer end of one of the support rods formed on the connector means as seen in FIG. 8. In this manner, the connector means is held in operative position so that it cannot move inwardly relative to the housing and so that the support rods are maintained in the desired position. Portion 210 also includes a handle portion thereon to facilitate grasping and moving the housing. The handle portion comprises an arcuate surface 220 on portion 210 and adapted to receive a person's thumb as well as a recessed surface 222 on portion 210 adapted to receive the rest of the fingers of a person's hand whereby the entire housing may be held in the hand. The bags 10, 12 and 14 in empty condition are shown in phantom lines in FIG. 8 to illustrate the manner in which the bags are supported in operative position on the support rods within the cartridge.

Referring now to FIGS. 10-14, a receptacle for use with the cartridge and adapted to connect the cartridge to an analytical instrument is illustrated. The receptacle comprises an integral body 230 of resilient material such as thermoplastic elastomer. As seen in FIG. 10, the body has a front surface 232 including a first plurality of recesses 234 formed therein and a second pair of recesses 236, these recesses being provided simply for the purpose of saving material. A protrusion 240 extends from surface 232 and is adapted to fit in a corresponding groove formed in an analytical instrument to properly position the receptacle relative to the instrument.

A cylindrical passage 242 is formed through body 230 and extends from front surface 232 to rear surface 244 of the body. Surface 244 joins with sloping surfaces 246 and 248 at the top and bottom of the rear side of the body. Passage 242 is adapted to receive the nose portion 126 of the connector means to guide the receptacle onto the connector means. A recess 250 is provided in rear surface 244. This recess enables one to see the groove in the nose portion to determine that the connector means and receptacle are properly seated relative to one another. Additionally, the recess is adapted to receive a person's finger so that when it is desired to disengage the receptacle from the connector means, a finger may be moved into the recess to engage the nose portion of an associated connector means to force the connector means away from the receptacle.

Six similar passages 260 are formed through the receptacle, and as seen in FIG. 14, each passage includes a first end 262 which is tapered and has a pair of seals in the form of spaced annular shoulders 264 and 266 which are adapted to engage and form a liquid tight seal with the six tapered bosses 122-132 formed on the connector means. When it is desired to interengage the receptacle with the connector means, the nose portion 140 of the connector is inserted through passage 242 until the groove 144 on the nose portion is visible within the recess 250, and when in this position, the tapered bosses 122-132 will be received within passages 260 and the outer surfaces of the bosses will be in sealing engagement with the sealing shoulders 264 and 266.

The opposite end 270 of each of the six passages 260 is in communication with the upper end of a plurality of similar grooves 274 formed in surface 244 of the receptacle. Each of these grooves receives a tube 276 similar to the tubes previously described and which are connected to an associated analytical instrument. These tubes are in liquid communication with ends 270 of passages 260 by means of conventional elbow connectors 280 having end portions 282 and 284 which have barb portions 286 and 288 formed therearound respectively to hold the elbow connectors in position and provide a liquid tight seal with passage 260 and tubes 276.

When a cartridge according to the invention is to be operatively connected with an analytical instrument, the receptacle is operatively connected with tubing from the instrument as shown in FIG. 14. The connector means is moved into operative relationship with the receptacle by inserting the nose portion and tapered bosses of the connector means into the appropriate passages provided through the receptacle. The entire assembly can be inserted into a cavity formed in the instrument with a single push, thereby simplifying this process. The cartridge may also be readily removed from the receptacle and disposed of when the fluids are depleted.

The invention has been described with reference to a preferred embodiment. Obviously, modifications, alterations and other embodiments will occur to others upon reading and understanding this specification. It is our intention to include all such modifications, alterations and alternate embodiments insofar as they come within the scope of the appended claims or the equivalent thereof.

What is claimed is:

1. A disposable liquid reagent cartridge for use with an analytical instrument comprising, a permanently closed hollow housing, bag means including a plurality of separate sealed flexible bags which are preformed independently of said housing and which are subject to damage and tampering if unprotected, at least some of said bags having reagents therein, means for supporting said bags in operative position within said housing, said housing being formed of a material sufficiently rigid to retain its outer shape and protect the bags supported therein from damage or tampering, connector means supported by said housing and being exposed to the exterior of said housing, and a flexible tube connected between each of said bags and said connector means to provide communication of said reagents between said bag means and said connector means.

2. A cartridge as defined in claim 1 wherein said bag means includes a bag having separate sealed chambers therein for receiving reagents.

3. A cartridge as defined in claim 1 wherein said housing has an outer configuration complementary to a cavity in an analytical instrument so that the casing fits within the cavity.

4. A cartridge as defined in claim 1 wherein said housing has a handle potion thereon to facilitate grasping and moving the housing.

5. A cartridge as defined in claim 1 wherein said housing includes a cover portion closing one side of the housing and having a first peripheral flange thereon, said housing including a second flange permanently bonded to said first flange.

6. A cartridge as defined in claim 5 wherein said cover portion has a deformed part adjacent said peripheral flange for fitting within said housing.

7. A cartridge as defined in claim 1 wherein said connector means includes support rod means extending therefrom within the housing, said bag means having support means thereon for engaging said support rod means to support the bag means in operative position.

8. A cartridge as defined in claim 7 wherein said support rod means includes a pair of support rods each including an outer end, said housing including a cover portion having recesses therein receiving and supporting each of the outer ends of the support rods.

9. A cartridge as defined in claim 7 wherein said support rod means includes a pair of support rods each of which has a tapered outer end for facilitating mounting of the bag means thereon, each support rod also having a tapered retainer portion thereon to retain the bag means on the support rods.

10. A cartridge as defined in claim 1 wherein said connector means includes a first plurality of tapered bosses thereon for connection to said flexible tube and a second plurality of tapered bosses thereon for connection to a receptacle, said first and second bosses being in communication with one another.

11. a cartridge as defined in claim 1 wherein said connector means includes an elongated rounded nose portion extending therefrom to facilitate insertion and removal of the connector means relative to a cooperating receptacle.

12. A cartridge as defined in claim 1 wherein said nose portion has a groove formed therein to indicate that the connector means is properly seated in a cooperating receptacle.

13. A disposable liquid reagent cartridge for use with an analytical instrument comprising, a permanently closed hollow housing, bag means including a plurality of separate sealed flexible bags which are preformed independently of said housing and which are subject to damage and tampering if unprotected, at least some of said bags having reagents therein, means for supporting said bags in operative position within said housing, said housing being formed of a material sufficiently rigid to retain its outer shape and protect the bags supported therein from damage or tampering, connector means supported by said housing and being exposed to the exterior of said housing, a flexible tube connected between each of said bags and said connector means to provide communication of said reagents between each of said bags and said connector means, said connector means including a first plurality of tapered bosses thereon for connection to said flexible tube and a second plurality of tapered bosses for connection to a receptacle, said first and second bosses being in communication with one another, and receptacle means including a plurality of openings receiving said second plurality of bosses to provide liquid communication and a liquid-tight seal between said second plurality of bosses and said openings, said receptacle including means in liquid communication with said openings and adapted to be connected with an analytical instrument.

* * * * *